(12) United States Patent
Wei

(10) Patent No.: US 12,247,987 B2
(45) Date of Patent: Mar. 11, 2025

(54) METHODS FOR DETECTION OF ABERRANT RESULTS CAUSED BY INCOMPLETE DISPERSION OF IMMUNOASSAY REAGENT

(71) Applicant: Siemens Healthcare Diagnostics Inc., Tarrytown, NY (US)

(72) Inventor: Tie Wei, Wilmington, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1100 days.

(21) Appl. No.: 17/250,347

(22) PCT Filed: Jun. 28, 2019

(86) PCT No.: PCT/US2019/039790
§ 371 (c)(1),
(2) Date: Jan. 8, 2021

(87) PCT Pub. No.: WO2020/014012
PCT Pub. Date: Jan. 16, 2020

(65) Prior Publication Data
US 2021/0270849 A1 Sep. 2, 2021

Related U.S. Application Data

(60) Provisional application No. 62/697,651, filed on Jul. 13, 2018.

(51) Int. Cl.
*G01N 33/72* (2006.01)
(52) U.S. Cl.
CPC .................. *G01N 33/723* (2013.01)
(58) Field of Classification Search
CPC .......................... G01N 33/723; G01N 33/541
See application file for complete search history.

(56) References Cited

U.S. PATENT DOCUMENTS

| 6,043,043 | A  | * | 3/2000  | Yip ..................... G01N 33/723 436/15 |
| 6,284,472 | B1 |   | 9/2001  | Wei et al. |
| 7,161,034 | B2 |   | 1/2007  | Chu et al. |
| 2005/0233398 | A1 | * | 10/2005 | Chu ..................... C07C 275/40 435/7.92 |
| 2009/0291464 | A1 | * | 11/2009 | Iwata ................. G01N 33/54313 435/29 |
| 2015/0044780 | A1 | * | 2/2015  | Kurz .................. G01N 33/6827 702/85 |
| 2022/0196640 | A1 | * | 6/2022  | Tyler ....................... G01N 21/82 |

FOREIGN PATENT DOCUMENTS

| CN | 104395728 | 3/2015 |
| CN | 107102153 | 8/2017 |
| JP | 857182168 | 9/1982 |
| JP | 2003329551 | 11/2003 |
| JP | 2015515005 | 5/2015 |

OTHER PUBLICATIONS

Bangs Laboratories Publication; "Ask The Particle Doctor"; Mar. 11, 2011; vol. 12, No. 1, 1-27. (Year: 2011).*
Abadie et al. Performance of the Roche Second Generation Hemoglobin A1c Immunoassay in the Presence of Hb-S or Hb-C. Annals of Clinical Laboratory Science 38 (1): 2008).*
Genc et al. Evaluation of Turbidimetric Inhibition Immunoassay (TINIA) and HPLC Methods for Glycated Haemoglobin Determination. Journal of Clinical Laboratory Analysis 26: 481-485 (2012).*
Schaible C et al: "B-477 Performance Evaluation of the Dimension Hemoglobin A1c Assay"; Clinical Chemistry; vol. 64; No. Suppl 1; Jan. 1, 2018; p. 288.
Cao Zheng et al: Have you stress tested your assay?; Practical Laboratory Medicine; vol. 5; Mar. 9, 2016; pp. 21-23.
Beckman Clouter: "HbA1c"; Hemoglobin A1c; B00389; Jul. 1, 2014; pp. 1-5.
Bangs Laboratories, Inc: TechNote 304, "Light-Scattering Assays"; Mar. 1, 2013; pp. 1-7.
Thaler, Leonard M., et al. "Diabetes in urban African-Americans. XVII. Availability of rapid HbA1c measurements enhances clinical decision-making." Diabetes care, 22.9 (1999): 1415-1421.
Miller, Christopher D., et al. "Rapid A1c availability improves clinical decision-making in an urban primary care clinic." Diabetes care, 26.4 (2003): 1158-1163.
Qu Hongyan et al:"Exploration of parameters for detecting antigen excess in automatic immunoturbidimetry", Chinese Journal of Practice Medicine, vol. 2, No. 5, p. 465-466, (2007), English Summary.
International Search Report for PCT/US2019/039790 dated Oct. 9, 2019.
Bangs Laboratories Publication; "Ask The Particle Doctor"; Mar. 11, 2011; vol. 12; No. 1; online] 1-27.

* cited by examiner

*Primary Examiner* — Gailene Gabel

(57) ABSTRACT

Methods of detecting and flagging and/or suppressing aberrant results caused by incomplete dispersion of an immunoassay reagent used in a turbidimetric immunoassay are disclosed.

23 Claims, 3 Drawing Sheets

FIG. 3

| Samples | 293nm-700nm | 340nm-700nm | Calculated 340nm-700nm | Calculated - measured 340nm-700nm | Difference>11.07 if yes, flag & suppress | %A1c Value |
|---|---|---|---|---|---|---|
| Calibrator L1 | 1435 | 221 | 224 | 3 | | |
| Calibrator L1 | 1406 | 208 | 203 | -5 | | |
| Calibrator L1 | 1407 | 209 | 204 | -5 | | |
| Calibrator L1 | 1415 | 210 | 209 | 0 | | |
| Calibrator L1 | 1414 | 210 | 209 | -1 | | |
| Calibrator L2 | 1373 | 179 | 179 | 0 | | |
| Calibrator L2 | 1379 | 187 | 184 | -3 | | |
| Calibrator L2 | 1371 | 178 | 178 | 0 | | |
| Calibrator L2 | 1368 | 178 | 176 | -2 | | |
| Calibrator L2 | 1373 | 180 | 179 | -1 | | |
| Calibrator L3 | 1314 | 135 | 137 | 3 | | |
| Calibrator L3 | 1323 | 139 | 143 | 4 | flag doesn't apply to calibration itself | |
| Calibrator L3 | 1315 | 134 | 138 | 4 | | |
| Calibrator L3 | 1322 | 139 | 143 | 4 | | |
| Calibrator L3 | 1317 | 134 | 140 | 6 | | |
| Calibrator L4 | 1248 | 88 | 90 | 3 | | |
| Calibrator L4 | 1244 | 87 | 87 | 1 | | |
| Calibrator L4 | 1243 | 86 | 87 | 1 | | |
| Calibrator L4 | 1245 | 89 | 88 | -1 | | |
| Calibrator L4 | 1245 | 86 | 88 | 2 | | |
| Calibrator L5 | 1221 | 71 | 71 | 0 | | |
| Calibrator L5 | 1219 | 71 | 69 | -2 | | |
| Calibrator L5 | 1220 | 71 | 70 | -1 | | |
| Calibrator L5 | 1218 | 74 | 69 | -5 | | |
| Calibrator L5 | 1217 | 72 | 68 | -4 | | |
| Sample | 1273 | 108 | 108 | 0 | No | 9.6 |
| Sample | 1295 | 108 | 123 | 16 | Yes, result flagged/suppressed | 8.8 |
| Sample | 1273 | 107 | 108 | 1 | No | 9.5 |
| Sample | 1272 | 107 | 107 | 0 | No | 9.6 |
| Sample | 1277 | 113 | 111 | -2 | No | 9.6 |
| Sample | 1273 | 109 | 108 | -1 | No | 9.6 |

METHODS FOR DETECTION OF ABERRANT RESULTS CAUSED BY INCOMPLETE DISPERSION OF IMMUNOASSAY REAGENT

CROSS REFERENCE TO RELATED APPLICATIONS/INCORPORATION BY REFERENCE STATEMENT

The subject application claims benefit under 35 USC § 119 (e) of U.S. provisional Application No. 62/697,651, filed Jul. 13, 2018. The entire contents of the above-referenced patent application are hereby expressly incorporated herein by reference entirety.

STATEMENT REGARDING FEDERALLY SPONSORED RESEARCH OR DEVELOPMENT

Not Applicable.

BACKGROUND

Accurate control of blood glucose can ameliorate much of the morbidity and mortality associated with diabetes mellitus. Therefore, many different assays for hemoglobin have been developed, based on the physical and chemical properties of hemoglobin or based on specific antibody-recognized epitopes thereof. Clinical studies have shown that HbA1c results improve decision making, patient compliance, and outcomes (Thaler et al. (1999) Diabetes Care, 22:1415-1421; and Miller et al. (2003) Diabetes Care, 26:1158-1163).

Immunoassays are currently the most common type of hemoglobin assay methods used in the clinical laboratory setting. These immunoassays utilize antibodies that recognize an epitope of hemoglobin, and in particular instances, an epitope of glycated hemoglobin (HbA1c), such as (but not limited to) at least a portion of the N-terminal glycated amino acids thereof. For example, the turbidimetric inhibition immunoassay (TINIA) for the analyte HbA1c utilizes an anti-HbA1c antibody and a polyhapten agglutinator (i.e., a synthetic molecule that contains multiple HbA1c epitopes to cause agglutination with free antibody). When no HbA1c analyte is present, the polyhapten reacts with free anti-HbA1c antibodies to form an insoluble antibody-polyhapten complex, and this results in turbidity and light scattering when the sample is illuminated with the light source. When the target analyte HbA1c is present in a biological sample (such as, but not limited to, a whole blood sample), the HbA1c analyte reacts with the anti-HbA1c antibody and forms a soluble analyte-antibody complex that reduces the amount of light scatter observed. The rate of the reaction can be measured turbidimetrically and is inversely proportional to the amount of HbA1c analyte present in the biological sample.

A major interferent to this assay is incompletely dispersed polyhapten reagent, which essentially mimics the insoluble antibody-polyhapten complex; incompletely dispersed polyhapten reagent causes light scattering that is subsequently measured turbidimetrically and thus translated into falsely low HbA1c values due to the inverse relationship between absorbance and analyte concentration. Therefore, new and improved methods of detecting and reducing the presence of aberrant results caused by incomplete dispersion of immunoassay reagents (such as, but not limited to, polyhapten reagents) are needed.

BRIEF DESCRIPTION OF THE DRAWINGS

FIG. 3 contains a chart illustrating one example of outlier flagging in accordance with the present disclosure, and as based on the results graphically depicted in FIG. 2.

DETAILED DESCRIPTION

Figure 1:
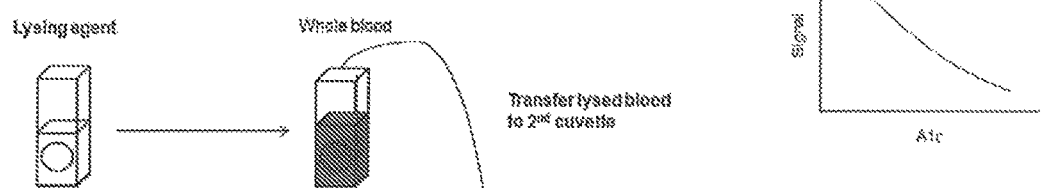
FIG. 1 schematically depicts a reaction scheme for a turbidimetric inhibition assay (TINIA) and identification of step at which one or more outlier(s) (imprecision(s)) happens.
Figure 1:
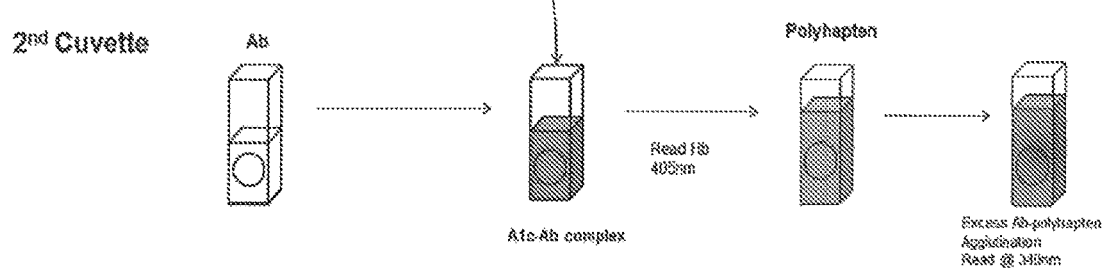
Figure 1:
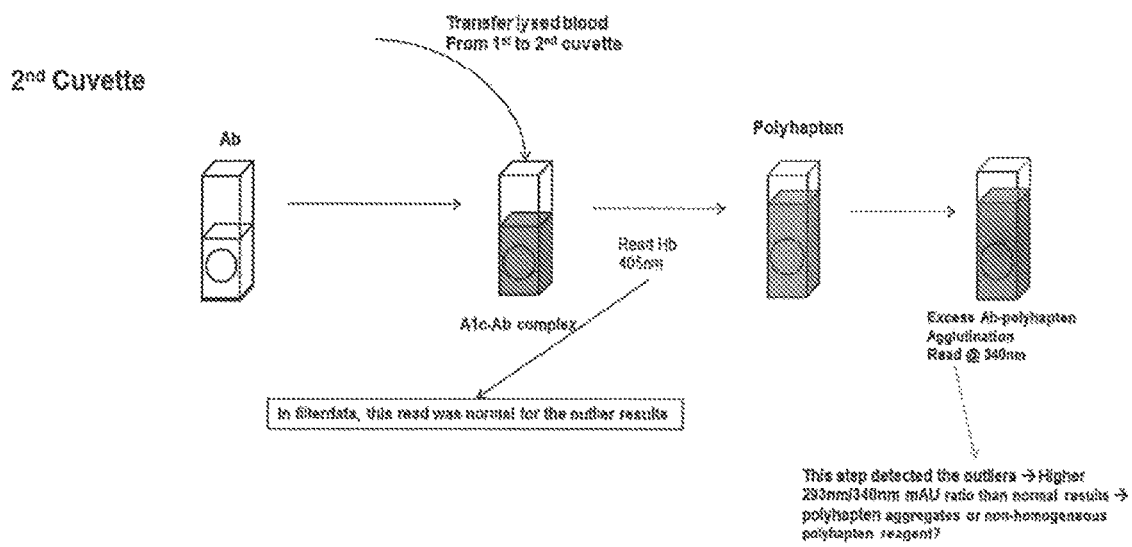

Before explaining at least one embodiment of the inventive concepts in detail by way of exemplary language and results, it is to be understood that the inventive concepts are not limited in their application to the details of construction and the arrangement of the components set forth in the following description. The inventive concepts are capable of other embodiments or of being practiced or carried out in various ways. As such, the language used herein is intended to be given the broadest possible scope and meaning, and the embodiments are meant to be exemplary—not exhaustive. Also, it is to be understood that the phraseology and terminology employed herein is for the purpose of description only and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, kits, and/or methods disclosed herein can be made and executed without undue experimentation in light of the present disclosure. While the articles, compositions, kits, and/or methods have been described in terms of particular embodiments, it will be apparent to those of skill in the art that variations may be applied to the articles, compositions, kits, and/or methods and in the steps or in the sequence of steps of the methods described herein without departing from the concept, spirit, and scope of the present disclosure. All such similar substitutions and modifications apparent to those skilled in the art are deemed to be within the spirit, scope, and concept of the inventive concepts as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety, and coating one moiety on another moiety, for example.

The term "sample" as used herein will be understood to include any type of biological sample that may be utilized in accordance with the present disclosure. Examples of fluidic biological samples that may be utilized include, but are not limited to, whole blood or any portion thereof (including, but not limited to, plasma or serum), whole or lysed blood cells (including, but not limited to, whole or lysed red blood cells), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, combinations thereof, and the like.

The term "target analyte-specific binding partner" as used herein will be understood to refer to any molecule capable of specifically associating with the target analyte. For example but not by way of limitation, the binding partner may be an antibody, a receptor, a ligand, aptamers, molecular imprinted polymers (i.e., inorganic matrices), combinations or derivatives thereof, as well as any other molecules capable of specific binding to the target analyte.

The term "antibody" is used herein in the broadest sense and refers to, for example, intact monoclonal antibodies and polyclonal antibodies, multi-specific antibodies (e.g., bispecific antibodies), antibody fragments and conjugates thereof that exhibit the desired biological activity of analyte binding (such as, but not limited to, Fab, Fab', F(ab')2, Fv, scFv, Fd, diabodies, single-chain antibodies, and other antibody fragments and conjugates thereof that retain at least a portion of the variable region of an intact antibody), antibody substitute proteins or peptides (i.e., engineered binding proteins/peptides), and combinations or derivatives thereof. The antibody can be of any type or class (e.g., IgG, IgE, IgM, IgD, and IgA) or sub-class (e.g., IgG1, IgG2, IgG3, IgG4, IgA1, and IgA2).

The term "hapten" as used herein refers to a small proteinaceous or non-protein antigenic determinant (or "epitope") which is capable of being recognized by a target analyte-specific binding partner, such as (but not limited to) an antibody. The term "polyhapten" as used herein will be understood to refer to a synthetic molecule that contains multiple epitopes/antigenic determinants attached thereto.

An "analyte" is a macromolecule that is capable of being recognized by a target analyte-specific binding partner, such as (but not limited to) an antibody. Both analytes and haptens comprise at least one antigenic determinant or "epitope," which is the region of the antigen or hapten which binds to the target analyte-specific binding partner (i.e., antibody). Typically, the epitope on a hapten is the entire molecule.

The term "reaction cuvette" as used herein includes any device(s) capable of performing at least one diagnostic assay as described herein. The reaction cuvette may perform the diagnostic assay(s) manually, but, in most instances, the reaction cuvette will be inserted into a system that automates the performance of the diagnostic assay(s). In one non-limiting embodiment, the reaction cuvette comprises a reaction cuvette for use in automated diagnostic assays conducted by, for example but not by way of limitation, one of the DIMENSION® integrated chemistry systems commercially available from Siemens Healthcare Diagnostics, Inc. (Newark, DE). However, it will be understood that the reaction cuvette can be any commercially available product or cuvette described or otherwise contemplated herein that is capable of performing one or more diagnostic assays in accordance with the present disclosure.

The term "turbidimetry" as used herein will be understood to refer to a process of measuring the loss of intensity of transmitted light due to the scattering effect of particles suspended in a solution. Light passed through a filter creates a light of known wavelength, which is then passed through a cuvette containing the test solution. A photoelectric cell collects the light which passes through the cuvette, and a measurement is then given for the amount of absorbed light. Thus, turbidimetry is a method for determining the concentration of a substance in a solution by the degree of cloudiness or turbidity the substance causes or by the degree of clarification it induces in a turbid solution.

Turning now to the inventive concepts, certain non-limiting embodiments of the present disclosure relate generally to kits, devices, and methods for improving the performance and reliability of immunoassays. In particular, certain embodiments of the present disclosure are related to kits, devices, and methods for detecting and flagging and/or suppressing aberrant results caused by incomplete dispersion of an immunoassay reagent.

Certain non-limiting embodiments of the present disclosure are directed to methods for detecting the presence and/or concentration of a target analyte in a biological sample. In certain particular (but non-limiting) embodiments, the methods may be further defined as methods of minimizing interference in immunoassays caused by incomplete dispersion of an immunoassay reagent.

The methods include combining, either simultaneously or wholly or partially sequentially: (1) a sample suspected of containing the target analyte; (2) at least one target analyte-specific binding partner (such as, but not limited to, an antibody); and (3) at least one immunoassay reagent capable of specifically binding to the target analyte-specific binding partner (such as, but not limited to, a polyhapten reagent or other type of incompletely dispersed particle agglutination assay reagent). The at least one target analyte-specific binding partner is then allowed to bind to the target analyte or the at least one immunoassay reagent.

In certain non-limiting embodiments, the signal generated by the immunoassay reagent may be detected via a turbidimetric (i.e., an agglutination) assay. The method also includes the use of dual calibrations (one for the analyte and another for the status of the at least one immunoassay reagent) that can be carried out for detecting abnormal results obtained for the analyte concentration. In a particular (but non-limiting) embodiment, the dual calibrations are carried out simultaneously in one single calibration event.

Any target peptide or protein analytes capable of detection via immunoassays may be detected via the methods of the present disclosure. Examples of target analytes include, but are not limited to, glycated hemoglobin (HbA1C), albumin, human chorionic gonadotropin (hCG), ferritin, growth hormone, prolactin, thyroglobulin (Tg), C-reactive protein (CRP), Rheumatoid Factor (RF), and the like.

Alternatively, the immunoassay may be a therapeutic drug monitoring (TDM) immunoassay that measures the serum level of a drug to ensure its concentration is within a therapeutic range therefor. Examples of target drug analytes capable of detection via TDM immunoassays include, but are not limited to, gentamicin, tobramycin, CRP, digoxin, amikacin, caffeine, carbamazepine, digitoxin, disopyramide, ethosuxamide, lidocaine, lithium methotrexate, NAPA, phenobarbital, phenytoin, primidone, procainamide, quinidine, theophylline, tobramycin, valproic acid, vancomycin, and the like.

Any biological sample known in the art for use with immunoassays as described herein may be utilized in accordance with the present disclosure. Examples of biological samples that may be utilized include, but are not limited to, urine, whole blood or any portion thereof (including, but not limited to, plasma or serum), whole (i.e., substantially unlysed) or lysed blood cells (including, but not limited to, whole or lysed red blood cells), saliva, sputum, cerebrospinal fluid (CSF), intestinal fluid, intraperitoneal fluid, cystic fluid, sweat, interstitial fluid, tears, mucus, bladder wash, semen, combinations, and the like.

In certain non-limiting embodiments, the present disclosure is directed to a method of detecting aberrant results caused by incomplete dispersion of a reagent used in a turbidimetric immunoassay. The method includes the following steps: (A) reacting, within a reaction cuvette, a biological sample suspected of containing a target analyte with a target analyte-specific binding partner, thereby forming a soluble analyte/target analyte-specific binding partner complex; (B) adding a polyhapten reagent to the reaction cuvette, wherein the polyhapten reagent reacts with excess target analyte-specific binding partner to form an insoluble polyhapten/target analyte-specific binding partner complex; (C) irradiating the reaction cuvette with light; (D) turbidimetrically detecting the insoluble polyhapten/target analyte-specific binding partner complex and undispersed polyhapten reagent in the reaction mixture by measuring an absorbance value at a first wavelength and an absorbance value at a second wavelength; (E) comparing the measured first and second wavelength absorbance values to predicted values of an established regression obtained from first and second wavelength absorbances at different analyte concentrations during assay calibration; and (F) flagging, as unacceptable, a concentration value for the target analyte obtained by a separate algorithm if the measured second wavelength absorbance value exceeds the predicted value by an established flag constant.

In certain non-limiting embodiments, the present disclosure is directed to a method of detecting aberrant results caused by incomplete dispersion of a reagent used in a turbidimetric immunoassay. The method includes the following steps: (A) reacting, within a reaction cuvette, a biological sample suspected of containing a target analyte with a target analyte-specific binding partner, thereby forming a soluble analyte/target analyte-specific binding partner complex; (B) adding a polyhapten reagent to the reaction cuvette, wherein the polyhapten reagent reacts with excess target analyte-specific binding partner to form an insoluble polyhapten/target analyte-specific binding partner complex; (C) irradiating the reaction cuvette with light; (D) turbidimetrically detecting the insoluble polyhapten/target analyte-specific binding partner complex and undispersed polyhapten reagent in the reaction mixture by measuring an absorbance value at a first wavelength and an absorbance value at a second wavelength; (E) comparing the measured first and second wavelength absorbance values to predicted values of an established regression obtained from first and second wavelength absorbances at different analyte concentrations during assay calibration; (F) flagging (as unacceptable) and suppressing a concentration value for the target analyte obtained by a separate algorithm if the measured second wavelength absorbance value exceeds the predicted value by an established flag constant; and (G) reporting a target analyte concentration if the measured second wavelength absorbance value does not exceed the predicted value by the established flag constant.

Any target analytes described or otherwise contemplated herein may be detected by the methods described herein. In certain particular (but non-limiting) embodiments of any of the above methods, the analyte is HbA1c, the antibody is an HbA1c antibody, and the polyhapten comprises a plurality of an HbA1c epitope.

In certain non-limiting embodiments, the present disclosure is directed to a method of detecting aberrant results caused by incomplete dispersion of a reagent used in a turbidimetric immunoassay. The method includes the following steps: (A) reacting, within a reaction cuvette, a biological sample suspected of containing a target analyte comprising glycated hemoglobin (HbA1c) with an HbA1c-specific binding partner (such as, but not limited to, an anti-HbA1c antibody to the target analyte), thereby forming a soluble HbA1c/HbA1c-specific binding partner complex (such as, but not limited to, a soluble HbA1c-antibody complex); (B) adding a polyhapten reagent to the reaction cuvette, wherein the polyhapten reagent reacts with excess HbA1c-specific binding partner (such as, but not limited to, anti-HbA1c antibody) to form an insoluble polyhapten/HbA1c-specific binding partner complex (such as, but not limited to, an insoluble polyhapten/anti-HbA1c antibody complex); (C) irradiating the reaction cuvette with light; (D) turbidimetrically detecting the insoluble polyhapten/HbA1c-specific binding partner complex and undispersed polyhapten reagent in the reaction mixture by measuring an absorbance value at a first wavelength and an absorbance value at a second wavelength; (E) comparing the measured first and second wavelength absorbance values to predicted values of an established regression obtained from first and second wavelength absorbances at different analyte concentrations during assay calibration; and (F) flagging, as unacceptable, a concentration value for the target analyte obtained by a separate algorithm if the measured second wavelength absorbance value exceeds the predicted value by an established flag constant.

In certain non-limiting embodiments, the present disclosure is directed to a method of detecting aberrant results caused by incomplete dispersion of a reagent used in a turbidimetric immunoassay. The method includes the following steps: (A) reacting, within a reaction cuvette, a biological sample suspected of containing a target analyte comprising glycated hemoglobin (HbA1c) with an HbA1c-specific binding partner (such as, but not limited to, an anti-HbA1c antibody to the target analyte), thereby forming a soluble HbA1c/HbA1c-specific binding partner complex (such as, but not limited to, a soluble HbA1c-antibody complex); (B) adding a polyhapten reagent to the reaction cuvette, wherein the polyhapten reagent reacts with excess HbA1c-specific binding partner (such as, but not limited to, anti-HbA1c antibody) to form an insoluble polyhapten/HbA1c-specific binding partner complex (such as, but not limited to, an insoluble polyhapten/anti-HbA1c antibody complex); (C) irradiating the reaction cuvette with light; (D) turbidimetrically detecting the insoluble polyhapten/HbA1c-specific binding partner complex and undispersed polyhapten reagent in the reaction mixture by measuring an absorbance value at a first wavelength and an absorbance value at a second wavelength; (E) comparing the measured first and second wavelength absorbance values to predicted values of an established regression obtained from first and second wavelength absorbances at different analyte concentrations during assay calibration; (F) flagging (as unacceptable) and suppressing a concentration value for the target analyte obtained by a separate algorithm if the measured second wavelength absorbance value exceeds the predicted value by an established flag constant; and (G) reporting a target analyte concentration if the measured second wavelength absorbance value does not exceed the predicted value by the established flag constant.

Any of the methods described or otherwise contemplated herein may further include the steps of lysing a biological sample in a first vessel/cuvette and then transferring the lysed biological sample to the reaction cuvette utilized in step (A).

Any wavelengths may be utilized as the first and second wavelengths in accordance with any of the methods of the present disclosure, so long as a relationship exists between the selected first and second wavelengths; this relationship provides an indication about polyhapten aggregation/dispersion, whereby a regression can be established at different analyte concentrations during assay calibration, thereby allowing for the establishment of a flag constant and thus detection of aberrant, outlier results when assaying biological samples. In particular, any wavelength may be utilized as the first wavelength so long as the wavelength can detect the presence of protein/peptide and thus can detect reagent dispersion and thereby provide an indication of the aggregation state of the polyhapten (or any other type of protein/polypeptide). Likewise, any wavelength may be utilized as the second wavelength so long as there is minimal protein/peptide detection at that wavelength; thus, any wavelength may be utilized as the second wavelength so long as the state of polyhapten dispersion has minimal effect on said wavelength, thereby allowing the second wavelength to serve as a control wavelength (i.e., a wavelength at which absorbance does not change as much as the first wavelength). For example (but not by way of limitation), the first wavelength may be in a range of from about 190 nm to about 300 nm, and the second wavelength may be in a range of from about 300 nm to about 650 nm. In a particular (but non-limiting) embodiment, the first wavelength is about 293 nm, and the second wavelength is about 340 nm.

In certain particular (but non-limiting) embodiments, step (D) of any of the above methods further comprises measuring a third wavelength; when present, the third wavelength simply serves as a "blanking wavelength" that ensures that the measurements of the first and second wavelengths are reliable and reproducible. In these embodiments, the absorbance at the first wavelength is a bichromatic value calculated as a first change in absorbance defined as ($mAU_{first\ wavelength}-mAU_{third\ wavelength}$), and the absorbance at the second wavelength is a bichromatic value calculated as a second change in absorbance defined as ($mAU_{second\ wavelength}-mAU_{third\ wavelength}$). Any wavelength that will serve as a "blanking wavelength" and allow for calculation of the bichromatic values described or otherwise contemplated herein can be utilized as the third wavelength in accordance with the present disclosure. Non-limiting examples of wavelengths that may be utilized as the third wavelength include those in a range of from about 600 nm to about 850 nm, including (but not limited to) about 600 nm, about 650 nm, about 700 nm, about 750 nm, about 800 nm, and about 850 nm.

In a particular (but non-limiting) embodiment, the third wavelength is 700 nm, and the absorbance at first wavelength is a bichromatic value calculated as a first change in absorbance defined as ($mAU_{293nm}-mAU_{700nm}$), and the absorbance at second wavelength is a bichromatic value calculated as a second change in absorbance defined as ($mAU_{340nm}-mAU_{700nm}$).

Any suitable regression analysis may be employed as the established regression in step (E) of the methods disclosed or otherwise contemplated herein. Non-limiting examples of regression analyses that can be utilized include linear regressions as well as non-linear regressions such as (but not limited to) logarithmic curves, exponential curves, hyperbolic curves, parabolic curves, sigmoidal curves, Michaelis Menten curves, polynomial curves, logistic regression (or logit) curves, and the like.

In certain non-limiting embodiments, the method further comprises the step of establishing the regression of step (E). This step includes performing an assay calibration by obtaining first and second wavelength absorbances at different known analyte concentrations and then establishing a regression therefrom. In a particular (but non-limiting) embodiment, the step of establishing a regression involves establishing regression coefficients (e.g., slope and intercept) that can be used to predict a normal absorbance value for the second wavelength based on each measured absorbance value for the first wavelength.

The term "established flag constant" as used herein refers to a value that is a cut-off beyond which a significant difference between the measured and predicted value calculated from a mathematical regression obtained during calibration using various calibration levels and replicates thereof is observed. The established flag constant represents a value that exceeds an acceptable variation margin/range for an absorbance obtained for a sample, based upon the sample's measured values when compared to the values predicted therefor from the regression analysis. The established flag constant may be any arbitrary numerical value that indicates the upper end of the acceptable variation margin/range, such as, but not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 6, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, and the like, or any non-integer value therebetween, or any slight variation in any of the values listed above (i.e., "about 11," about 15," etc.). Alternatively, the established flag constant may be a percentage that indicates the upper end of the acceptable variation margin/range, such as, but not limited to, 5000%, 4000%, 3000%, 2000%, 1000%, 900%, 800%, 700%, 600%, 500%, 450%, 400%, 350%, 300%, 250%, 200%, 150%, 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, and the like, or any integer or non-integer percentage value therebetween, or any slight variation in any of the percentage values listed above (i.e., "about 85%," about 70%," etc.).

In certain non-limiting embodiments, the measurements obtained in the methods of detecting aberrant results described or otherwise contemplated herein are measured and calculated independent of the actual assay for target analyte presence and/or concentration in the biological sample. Alternatively, one or more of the measurements obtained by the methods described and/or contemplated herein may be utilized in the actual assays for target analyte presence and/or concentration in the biological sample.

In certain non-limiting embodiments, when one or more values is flagged (or flagged and suppressed) in step (F), the method may further comprise the step of instructing a user to increase mixing of the polyhapten reagent and to then repeat the assay steps (A)-(F).

It will be understood that, while the methods are described herein above for use with a polyhapten reagent, the methods of detecting aberrant results of the present disclosure are also applicable to use with other types of incompletely dispersed particle agglutination assay reagents. Therefore, the scope of the present disclosure further includes any and all variations of the methods described herein above where the term "polyhapten reagent" is replaced with "particle agglutination assay reagent."

Any of the method steps described herein may be performed, for example but not by way of limitation, by a user. However, as used herein, the term "user" is not limited to use by a human being; rather, the term "user" may comprise (for example, but not by way of limitation) a computer, a server, a website, a processor, a network interface, a human, a user terminal, a virtual computer, combinations thereof, and the like.

The various embodiments of the present disclosure may be utilized with any reflectance spectroscopic diagnostic instrument that is capable of (or has been modified to be capable of) functioning in accordance with the methods described herein. In certain, non-limiting embodiments, the instrument may be a point of care instrument. The reflectance spectroscopic diagnostic instrument may be a system or systems that are able to embody and/or execute the logic of the methods/processes described herein. Logic embodied in the form of software instructions and/or firmware may be executed on any appropriate hardware. For example, logic embodied in the form of software instructions and/or firmware may be executed by one or more components on a dedicated system or systems, on a personal computer system, on a distributed processing computer system, and/or the like. In some embodiments, the entire logic may be implemented in a stand-alone environment operating on an instrument (such as, but not limited to, a point of care instrument). In other embodiments, the logic may be implemented in a networked environment such as a distributed system in which multiple instruments collect data that is transmitted to a centralized computer system for analyzing the data and supplying the results of the analysis to the instruments. Each element of the instrument may be partially or completely network-based or cloud based, and may or may not be located in a single physical location.

Circuitry used herein includes (but is not limited to) analog and/or digital components, or one or more suitably programmed processors (e.g., microprocessors) and associated hardware and software, or hardwired logic. Also, "components" may perform one or more functions. The term "component" may include hardware, such as but not limited to, a processor (e.g., microprocessor), an application specific integrated circuit (ASIC), field programmable gate array (FPGA), a combination of hardware and software, and/or the like.

Software utilized herein may include one or more computer readable medium (i.e., computer readable instructions) that when executed by one or more components cause the component to perform a specified function. It should be understood that the algorithms described herein may be stored on one or more non-transient memory. Non-limiting exemplary non-transient memory may include random access memory, read only memory, flash memory, and/or the like. Such non-transient memory may be electrically based, optically based, and/or the like.

Certain non-limiting embodiments of the present disclosure are directed to reagent kits useful for conveniently performing the immunoassay methods described herein above. The reagent kit includes at least one target-analyte specific binding partner (such as, but not limited to, an antibody against the target analyte) and at least one polyhapten reagent, each as described in detail herein above.

Certain other non-limiting embodiments of the present disclosure are directed to an immunoassay device (such as, but not limited to, an immunoassay cartridge) which contain the reagent kits described herein above and which are for use in the immunoassay methods described herein above. For example, the immunoassay device may include at least one compartment capable of receiving a sample suspected of containing the target peptide or protein analyte, wherein the at least one compartment includes at least one target analyte-specific binding partner (such as, but not limited to, an antibody against the target analyte) as described in detail herein above and at least one polyhapten reagent as described in detail herein above.

In addition, the reagent kits and/or immunoassay devices of the present disclosure may further contain other component(s) and/or reagent(s) for conducting any of the particular immunoassays described or otherwise contemplated herein. The nature of these additional component(s)/reagent(s) will depend upon the particular immunoassay format, and identification thereof is well within the skill of one of ordinary skill in the art. Examples of additional reagents/components that may be present in the reagent kits and/or immunoassay devices of the present disclosure include, but are not limited to, diluents, lysing agents (for lysing red blood cells), wash solutions (such as but not limited to, isotonic solutions), positive controls, negative controls, quality controls, and/or actuators, as well as any combination thereof.

The relative amounts of the various components/reagents in the kits and/or immunoassay devices can vary widely to provide for concentrations of the components/reagents that substantially optimize the reactions that need to occur during the assay methods and further to optimize substantially the sensitivity of an assay.

The reagent kits of the present disclosure may further include a set of written instructions explaining how to use the kit. A kit of this nature can be used with any of the immunoassay devices and/or in any of the methods described or otherwise contemplated herein.

The immunoassay device may have one or more manual functions associated therewith (i.e., wherein pipetting is required for addition of one or more reagents and/or movement of a mixture between two compartments); alternatively, the immunoassay device may be a fully automatic, closed system in which the necessary reagents/components are disposed in various compartments during construction of the immunoassay device (wherein the various compartments are in continuous fluidic communication (or are capable of being in continuous fluidic communication)), and thus no manual manipulation of the sample and/or reagent(s) is required for performance of the assay after the sample is added to the immunoassay device.

The immunoassay device comprises one or more compartments containing the components/reagents described herein above; the immunoassay device may be provided with any number of compartments, any arrangement of compartments, and any distribution of the components/reagents therebetween, so long as the device is able to function in accordance with the present disclosure. When provided with multiple compartments, the compartments may be completely separated from one another, or one or more compartments may be capable of being in fluidic communication with one another. Various structures of immunoassay devices that are capable of use in accordance with the present disclosure are well known in the art, and therefore no further description thereof is deemed necessary.

In certain embodiments, the immunoassay device includes at least first and second compartments. The first compartment is capable of receiving a biological sample and, if desired (but not by way of limitation), may include a mechanism for separating protein/peptide from the bulk of the sample, lysing red blood cells, etc. Said separation mechanisms are well known in the art of immunoassay devices, and therefore no further description thereof is deemed necessary. The second compartment is capable of being in fluidic communication with the first compartment and includes the at least one target analyte-specific binding partner (such as, but not limited to, an antibody against the target analyte) and/or the at least one immunoassay reagent for performing the immunoassay methods described in detail herein above. Alternatively, the immunoassay device may include a third compartment for storage of the at least one immunoassay reagent, and wherein the at least one immunoassay reagent can be transferred from the third compartment into the second compartment.

The immunoassay device may also include an optical read chamber that is capable of being optically interrogated by a spectrometer. The optical read chamber may be associated with any of the compartments described herein above, or the optical read chamber may be associated with a separate compartment from those described herein above.

The inlet channel and a compartment, as well as two compartments, may be described as being "capable of being in fluidic communication" with one another; this phrase indicates that the compartment(s) may still be sealed, but the two compartments are capable of having fluid flow therebetween upon puncture of a seal formed therein or therebetween.

The kits/immunoassay devices of the present disclosure may be provided with any other desired features known in the art or otherwise contemplated herein. For example, but not by way of limitation, the kits/immunoassay devices of the present disclosure may further include one or more additional compartments containing other solutions, such as but not limited to, lysing agents (for lysing red blood cells), diluents, wash solutions, labeling agents, interference solutions, positive controls, negative controls, quality controls, and/or actuators, as well as any combination thereof.

Examples

An Example is provided hereinbelow. However, the present disclosure is to be understood to not be limited in its application to the specific experimentation, results, and laboratory procedures disclosed herein. Rather, this Example is simply provided as one of various embodiments and is meant to be exemplary, not exhaustive.

Incomplete dispersion of a polyhapten reagent for a turbidimetric immunoassay, even with optimized mixing parameters, results in aberrant immunoassay results. The aberrant results are high absorbance outliers, which are translated into falsely low analyte values due to the inverse relationship between absorbance and analyte value. For example, falsely low HbA1c results not only make the immunoassay imprecise but may also cause misdiagnosis and incorrect assessment of blood glucose control in diabetic patients.

Attempts to overcome this issue have included optimizing the mixing parameters used when the polyhapten reagent is present; use of the optimized mixing parameters greatly reduced the frequency of this type of outlier by about 5-10 fold. However, optimizing the mixing parameters was not sufficient to solve the problem of aberrant immunoassay results. Attempts to further optimize the mixing parameters didn't result in a reduction in outliers, and the frequency of outliers is still about 1/750 (0.13%), even when the optimized mixing parameters are utilized.

Thus, the present disclosure is directed to methods of detecting aberrant results caused by incomplete dispersion of an immunoassay reagent (such as, but not limited to, a polyhapten reagent). Although the incomplete polyhapten dispersion is not prevented, the present disclosure provides methods and procedures for detecting the incomplete dispersion of the immunoassay reagent using wavelength absorbance information and then flagging and suppressing any outlier results.

By flagging and suppressing the outliers, the precision of the immunoassay is improved, and misdiagnosis is avoided, along with (for example, but not by way of limitation) incorrect assessment of glucose control. By the methods of the present disclosure, the frequency of outliers is reduced from 0.13% to 0.006%, which is an over 20 fold decrease.

Incomplete dispersion of the polyhapten reagent leaves a footprint in mAU (milliabsorption units). This footprint occurs when the polyhapten aggregates are not well dispersed, and the footprint was observed (in one non-limiting embodiment) as the polyhapten reagent generating a higher 293 nm/340 nm absorbance ratio than the well dispersed reagent. Based on this feature, the regression between normal 293 nm and 340 nm absorbance can be established at different analyte concentrations from the assay calibration, and then the regression statistics can be utilized to test the 293 nm versus 340 nm absorbance for each test sample. When the 293 nm versus 340 nm ratio is consistent with the normal regression, the test result is acceptable; otherwise, polyhapten aggregates are detected, and the result is flagged and suppressed.

In the present disclosure, the utilization of dual calibrations—one for the analyte and one for the status of a reagent in the reaction mixture—are thus carried out simultaneously in one single calibration event. Abnormality of the reagent's status is detected by applying the parameters established from its calibration.

FIG. 1 provides a reaction scheme for a turbidimetric inhibition assay (TINIA). In the assay, whole blood is mixed with a lysing agent (see upper panel, row labeled as "$1^{st}$ Cuvette"), and then the lysed blood is transferred to a second cuvette that contains antibody for the analyte (such as, but not limited to, HbA1c) to be detected (see upper panel, row labeled as "$2^{nd}$ Cuvette"). The cuvette containing the antibody-antigen complex (such as, but not limited to, a HbA1c-Ab complex) is then read at 405 nm, and the polyhapten reagent is subsequently added. After incubation, excess antibody-polyhapten agglutination is read at 340 nm. The lower panel identifies the step at which outlier (imprecision) happens and can be detected.

Figure 2:
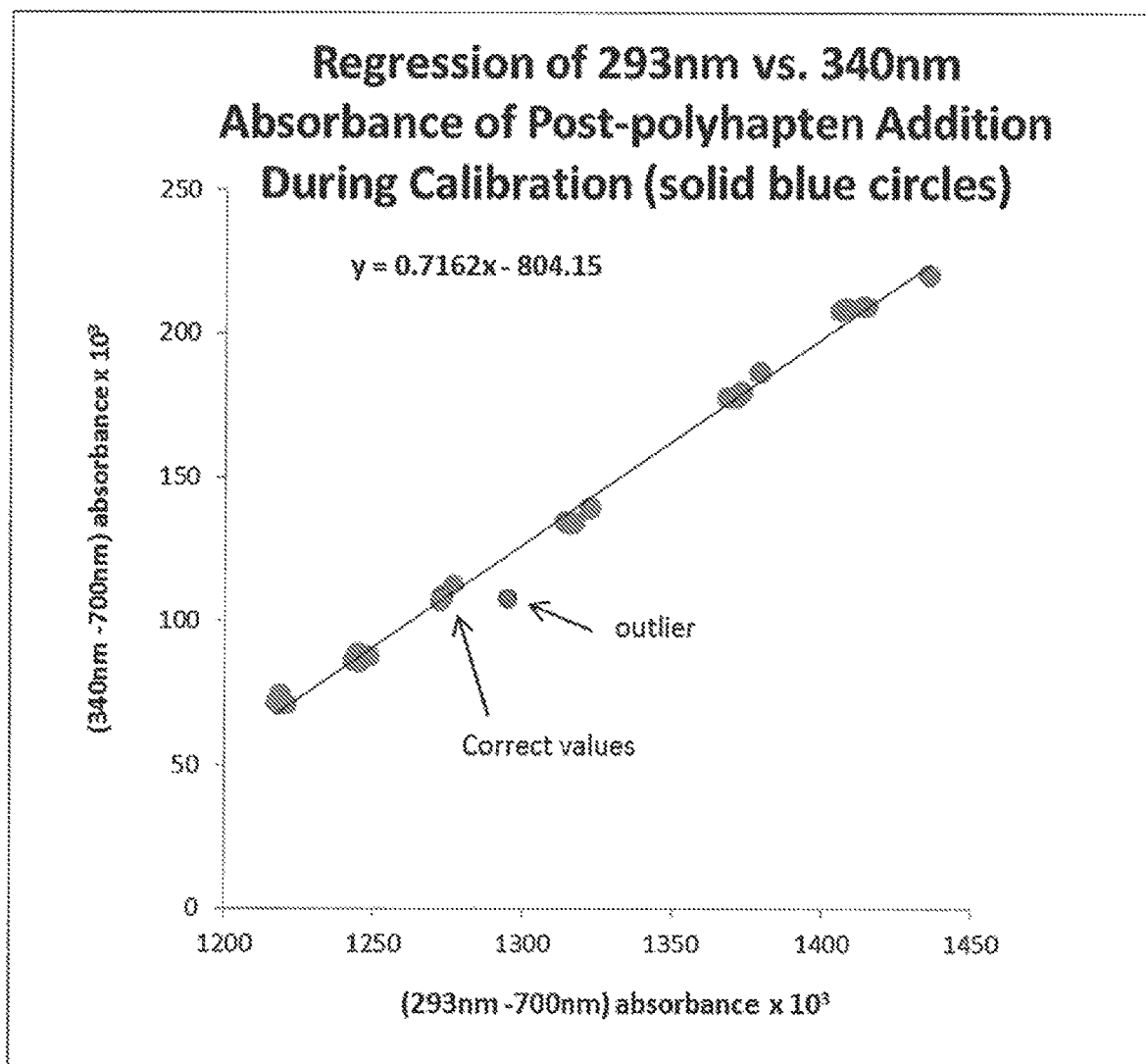
FIG. 2 graphically depicts calibration of normal 293 nm versus 340 nm regression of post-polyhapten addition (solid blue circles) and outlier detection (red circle) and suppression.

FIG. 2 graphically depicts calibration of normal 293 nm versus 340 nm regression of post-polyhapten addition (solid blue circles) and outlier detection (red circle) and suppression, as described herein below.

Following addition of polyhapten reagent and mixing, photometric reads of the reaction mixture were taken on a DIMENSION® instrument (Siemens Healthcare Diagnostics, Inc., Newark, DE). Using the photometric reads obtained during calibration, a linear regression was performed between the bichromatic absorbance at 340 nm and 293 nm for all five calibrator levels of five replicates. The slope (α) and intercept (B) of this regression were then generated and stored for the 340 nm and 293 nm to define their normal relationship based on the following formula:

$$mAU_{340nm} - mAU_{700nm} = \alpha \cdot (mAU_{293nm} - mAU_{700nm}) + \beta.$$

Then α and β were used with ($mAU_{293nm} - mAU_{700nm}$) obtained from the sample test to predict the bichromatic $mAU_{340nm}$ (i.e., $mAU_{340nm} - mAU_{700nm}$). If the bichromatic $mAU_{340nm}$ for a sample test was lower than predicted by a certain margin, the flag was tripped. During sample testing:

(1) Retrieve α and β from calibration;
(2) Use α and β to flag polyhapten under-mix;
(3) If (bichromatic $mAU_{340nm\_predicted}$ − bichromatic $mAU_{340nm\_measured}$) ≥ C, then flag;
(4) Where bichromatic $mAU_{340nm\_measured} = mAU_{340nm\_measured} - mAU_{700nm\_measured}$), and
(5) Where C is a constant of 11.0 that was established based on the data analysis shown in FIG. 2.

In FIG. 2, all % HbA1c outliers from a study were inspected to see if the outliers were associated with a large distance between the regression line and the measured 340 nm. The point of interception between the measured 340 nm and the regression line is the predicted (or normal) value for 340 nm obtained from the calibration and indicates substantially where the measured 340 nm value should fall. As can be seen, most % HbA1c results followed this rule (green circles). However, when the measured 340 nm value deviated too far from the regression line, the % HbA1c result is an outlier (red circle).

It was determined that if the established flag constant (C) was positioned at 11.0 (i.e., the distance between the red circle and the regression line), the vast majority of low % HbA1c outliers were flagged, while the "good" % HbA1c results were not mistakenly flagged. However, if C was positioned at a lower value (i.e., at 5.0), some of the "good" % HbA1c results were incorrectly flagged. This is because the regression line is not exact, and there is some noise associated with the regression analysis other than non-dispersion of the polyhapten reagent. Therefore, the flag constant must be positioned sufficiently high enough to overcome any noise associated with the assay/regression analysis.

FIG. 3 contains a chart illustrating one example of outlier flagging in accordance with the present disclosure, and as based on the results graphically depicted in FIG. 2. In this Example of outlier flagging, 8.8% A1c was a flagged outlier because its calculated ($mAU_{340nm}$–$mAU_{700nm}$)–measured ($mAU_{340nm}$–$mAU_{700nm}$) is equal to 16, which exceeded the established flag constant of 11.0. Bichromatic reads were used here to correct absorbance measurement inconsistency due to imperfections of photometer positioning and cuvetted surface.

Thus, in accordance with the present disclosure, there have been provided compositions, kits, and devices, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the presently disclosed inventive concepts.

What is claimed is:

1. A method of detecting aberrant results caused by incomplete dispersion of a polyhapten reagent used in a turbidimetric HbA1c immunoassay, the method comprising the steps of:
   (A) reacting, within a reaction cuvette, a biological sample suspected of containing a target analyte comprising glycated hemoglobin (HbA1c) with an anti-HbA1c antibody to the target analyte, thereby forming a soluble HbA1c-antibody complex;
   (B) adding a polyhapten reagent to the reaction cuvette, wherein the polyhapten reagent reacts with excess anti-HbA1c antibody to form an insoluble polyhapten/target analyte-specific binding partner polyhapten/anti-HbA1c antibody complex;
   (C) irradiating the reaction cuvette with light at a first wavelength and a second wavelength;
   (D) turbidimetrically detecting the insoluble polyhapten/target analyte-specific binding partner polyhapten/anti-HbA1c antibody complex and undispersed polyhapten reagent in the reaction mixture by measuring an absorbance value at the first wavelength and an absorbance value at the second wavelength;
   (E) comparing the measured first and second wavelength absorbance values to predicted values of an established regression obtained from first and second wavelength absorbances at known HbA1c control values for the target analyte having different concentrations during assay calibration; and
   (F) flagging, as unacceptable, a concentration value for the target analyte HbA1c obtained by a separate algorithm if the measured second wavelength absorbance value exceeds the predicted value by an established flag constant.

2. The method of claim 1, wherein the first wavelength is in a range of from about 190 nm to about 300 nm, and the second wavelength is in a range of from about 300 nm to about 650 nm, and wherein the first wavelength is different from the second wavelength.

3. The method of claim 2, wherein the first wavelength is about 293 nm, and the second wavelength is about 340 nm.

4. The method of claim 1, further comprising measuring a third wavelength, and wherein the absorbance at first wavelength is a bichromatic value calculated as a first change in absorbance defined as ($mAU_{first\ wavelength}$–$mAU_{third\ wavelength}$), and the absorbance at second wavelength is a bichromatic value calculated as a second change in absorbance defined as ($mAU_{second wavelength}$–$mAU_{third wavelength}$).

5. The method of claim 4, wherein the third wavelength is in a range of from about 600 nm to about 850 nm.

6. The method of claim 1, further comprising the step of establishing the regression of (E).

7. The method of claim 1, wherein the regression of (E) is a linear regression.

8. The method of claim 1, wherein step (F) is further defined as flagging and suppressing a concentration value for the target analyte HbA1c obtained by a separate algorithm if the measured second wavelength absorbance value exceeds the predicted value by an established flag constant, and wherein the method further comprises the step of:
   (G) reporting a HbA1c concentration if the measured second wavelength absorbance value does not exceed the predicted value by the established flag constant.

9. The method of claim 1, wherein the first wavelength is in a range of from about 190 nm to 300 nm, and the second wavelength is in a range of from 300 nm to about 650 nm, and wherein the first wavelength is different from the second wavelength.

10. The method of claim 1, wherein the first wavelength is about 293 nm, and the second wavelength is about 340 nm, and wherein "about" is defined as a variation of up to ±5%.

11. The method of claim 10, wherein the first wavelength is 293 nm, and the second wavelength is 340 nm.

12. A method of detecting aberrant results caused by incomplete dispersion of a polyhapten reagent used in a turbidimetric HbA1c immunoassay, the method comprising the steps of:
   (A) reacting, within a reaction cuvette, a biological sample suspected of containing a target analyte comprising glycated hemoglobin (HbA1c) with an anti-HbA1c antibody to the target analyte, thereby forming a soluble HbA1c antibody HbA1c/anti-HbA1c antibody complex;
   (B) adding a polyhapten reagent to the reaction cuvette, wherein the polyhapten reagent reacts with excess anti-HbA1c antibody to form an insoluble polyhapten/target analyte-specific binding partner polyhapten/anti-HbA1c antibody complex;
   (C) irradiating the reaction cuvette with light at a first wavelength and a second wavelength;
   (D) turbidimetrically detecting the insoluble polyhapten/target analyte-specific binding partner polyhapten/anti-HbA1c antibody complex and undispersed polyhapten reagent in the reaction mixture by measuring an absorbance value at the first wavelength and an absorbance value at the second wavelength;

(E) comparing the measured first and second wavelength absorbance values to predicted values of an established regression obtained from first and second wavelength absorbances at known HbA1c control values for the target analyte having different concentrations during assay calibration;

(F) flagging and suppressing a concentration value for the target analyte HbA1c obtained by a separate algorithm if the measured second wavelength absorbance value exceeds the predicted value by an established flag constant; and (G) reporting a target analyte an HbA1c concentration if the measured second wavelength absorbance value does not exceed the predicted value by the established flag constant.

13. The method of claim 12, wherein:
(i) the first wavelength is in a range of from about 190 nm to about 300 nm, and the second wavelength is in a range of from about 300 nm to about 650 nm, and wherein the first wavelength is different from the second wavelength; and
(ii) the regression of (E) is a linear regression.

14. The method of claim 12, wherein the first wavelength is in a range of from about 190 nm to about 300 nm, and the second wavelength is in a range of from about 300 nm to about 650 nm, and wherein the first wavelength is different from the second wavelength.

15. The method of claim 14, wherein the first wavelength is about 293 nm, and the second wavelength is about 340 nm.

16. The method of claim 12, further comprising measuring a third wavelength, and wherein the absorbance at first wavelength is a bichromatic value calculated as a first change in absorbance defined as ($mAU_{first\ wavelength} - mAU_{third\ wavelength}$), and the absorbance at second wavelength is a bichromatic value calculated as a second change in absorbance defined as ($mAU_{second\ wavelength} - mAU_{third\ wavelength}$).

17. The method of claim 16, wherein the third wavelength is in a range of from about 600 nm to about 850 nm.

18. The method of claim 12, further comprising the step of establishing the regression of (E).

19. The method of claim 12, wherein the regression of (E) is a linear regression.

20. The method of claim 12, wherein step (F) is further defined as flagging and suppressing a concentration value for the target analyte obtained by a separate algorithm if the measured second wavelength absorbance value exceeds the predicted value by an established flag constant, and wherein the method further comprises the step of:

(G) reporting a target analyte concentration if the measured second wavelength absorbance value does not exceed the predicted value by the established flag constant.

21. The method of claim 12, wherein the first wavelength is in a range of from about 190 nm to 300 nm, and the second wavelength is in a range of from 300 nm to about 650 nm, and wherein the first wavelength is different from the second wavelength.

22. The method of claim 12, wherein the first wavelength is about 293 nm, and the second wavelength is about 340 nm, and wherein "about" is defined as a variation of up to ±5%.

23. The method of claim 22, wherein the first wavelength is 293 nm, and the second wavelength is 340 nm.

* * * * *